US009241800B2

(12) United States Patent
Gustilo et al.

(10) Patent No.: US 9,241,800 B2
(45) Date of Patent: Jan. 26, 2016

(54) TIBIAL COMPONENT WITH A CONVERSION MODULE FOR A KNEE IMPLANT

(75) Inventors: Ramon B. Gustilo, Eden Prairie, MN (US); Jude L. Sasing, Quezon (PH); Richard Raymond N. Dimagiba, Paranaque (PH)

(73) Assignee: Orthopaedic International Inc. (PH)

( * ) Notice: Subject to any disclaimer, the term of this patent is extended or adjusted under 35 U.S.C. 154(b) by 1636 days.

(21) Appl. No.: 11/643,273

(22) Filed: Dec. 21, 2006

(65) Prior Publication Data

US 2007/0179627 A1 Aug. 2, 2007

Related U.S. Application Data

(60) Provisional application No. 60/752,849, filed on Dec. 21, 2005.

(51) Int. Cl.
*A61F 2/38* (2006.01)
*A61F 2/30* (2006.01)

(52) U.S. Cl.
CPC .............. *A61F 2/389* (2013.01); *A61F 2/30734* (2013.01); *A61F 2002/30383* (2013.01); *A61F 2002/30385* (2013.01); *A61F 2002/30387* (2013.01); *A61F 2002/30736* (2013.01)

(58) Field of Classification Search
CPC ................................ A61F 2/3868; A61F 2/389
USPC .......... 623/20.14–20.16, 20.32–20.34, 20.21, 623/20.28, 20.31
See application file for complete search history.

(56) References Cited

U.S. PATENT DOCUMENTS

| | | | |
|---|---|---|---|
| 5,194,066 A * | 3/1993 | Van Zile | 623/20.15 |
| 5,358,529 A | 10/1994 | Davidson | |
| 5,370,699 A * | 12/1994 | Hood et al. | 623/20.28 |
| 5,417,694 A | 5/1995 | Marik et al. | |
| 5,458,637 A * | 10/1995 | Hayes | 623/16.11 |
| 5,474,555 A | 12/1995 | Puno et al. | |
| 5,514,140 A | 5/1996 | Lackey | |
| 5,549,688 A | 8/1996 | Ries et al. | |
| 5,549,702 A | 8/1996 | Ries et al. | |
| 5,549,703 A | 8/1996 | Daigle et al. | |
| 5,560,096 A | 10/1996 | Stephens | |
| 5,569,261 A | 10/1996 | Marik et al. | |

(Continued)

FOREIGN PATENT DOCUMENTS

FR 2748389 A1 * 11/1997 .............. A61F 2/38

OTHER PUBLICATIONS

Translation of FR2748389A1, retrieved from espacenet on Apr. 17, 2015.*

*Primary Examiner* — Thomas J Sweet
*Assistant Examiner* — Megan Wolf
(74) *Attorney, Agent, or Firm* — Kagan Binder, PLLC

(57) ABSTRACT

A tibial prosthesis including a tibial component including a tray having first and second opposing surfaces and a stem extending from the second surface of the tibial component, a tibial conversion module including a receiver portion defining a stem-receiving cavity for slideable engagement with the stem of the tibial component, wherein the stem of the tibial component is positioned within the stem-receiving cavity at a first end of the receiver portion, and an extension peg engaged with the stem-receiving cavity at a second end of the receiver portion that is opposite the first end of the receiver portion.

17 Claims, 6 Drawing Sheets

(56) References Cited

U.S. PATENT DOCUMENTS

| | | |
|---|---|---|
| 5,575,793 A | 11/1996 | Carls et al. |
| 5,578,039 A | 11/1996 | Vendrely et al. |
| 5,593,449 A | 1/1997 | Roberson, Jr. |
| 5,609,641 A | 3/1997 | Johnson et al. |
| 5,609,642 A | 3/1997 | Johnson et al. |
| 5,628,749 A | 5/1997 | Vendrely et al. |
| 5,665,088 A | 9/1997 | Gil et al. |
| 5,766,257 A * | 6/1998 | Goodman et al. ......... 623/20.21 |
| 5,824,105 A | 10/1998 | Ries et al. |
| 5,879,394 A | 3/1999 | Ashby et al. |
| 6,067,701 A | 5/2000 | Vandewalle |
| 6,139,581 A | 10/2000 | Engh et al. |
| 6,146,424 A | 11/2000 | Gray, Jr. et al. |
| 6,162,255 A | 12/2000 | Oyola |
| 6,214,052 B1 | 4/2001 | Burkinshaw |
| 6,228,091 B1 | 5/2001 | Lombardo et al. |
| RE37,277 E | 7/2001 | Baldwin et al. |
| 6,428,577 B1 | 8/2002 | Evans et al. |
| 6,824,566 B2 | 11/2004 | Kana et al. |
| 2003/0204263 A1* | 10/2003 | Justin et al. ................. 623/20.15 |
| 2005/0154470 A1* | 7/2005 | Sekel ......................... 623/20.15 |

* cited by examiner

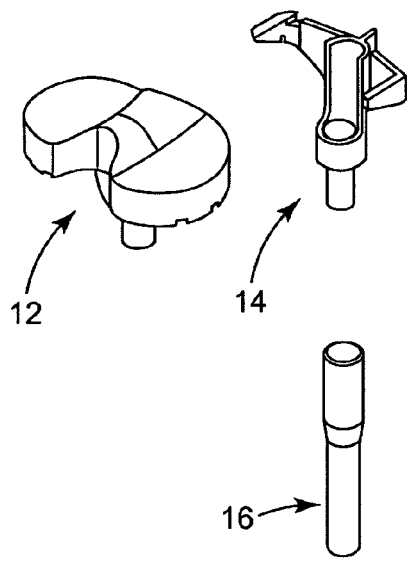
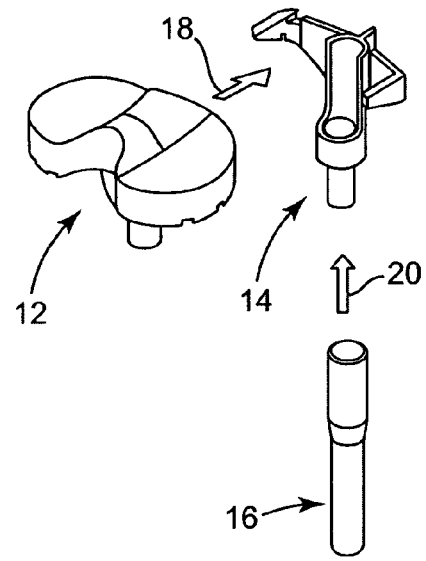
Fig. 1  Fig. 2
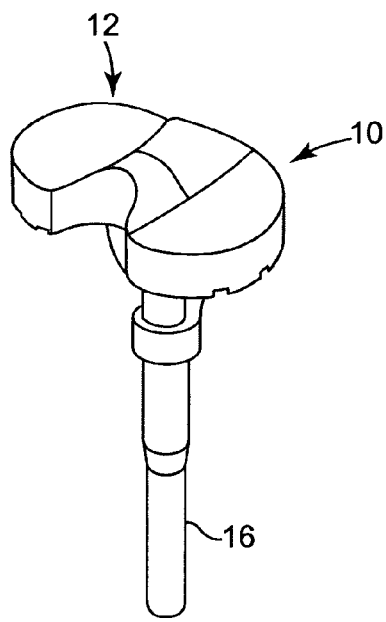
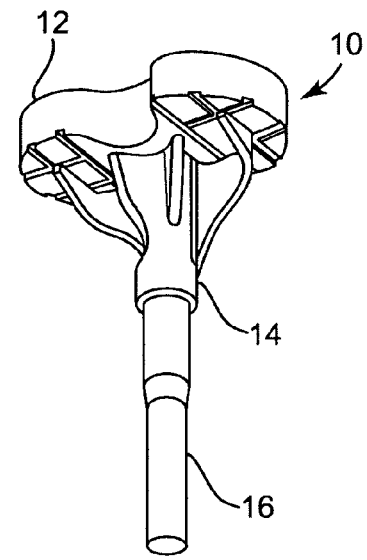
Fig. 3a  Fig. 3b

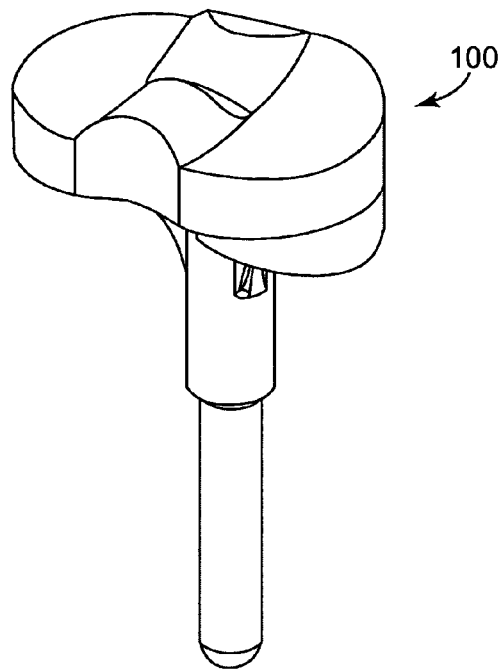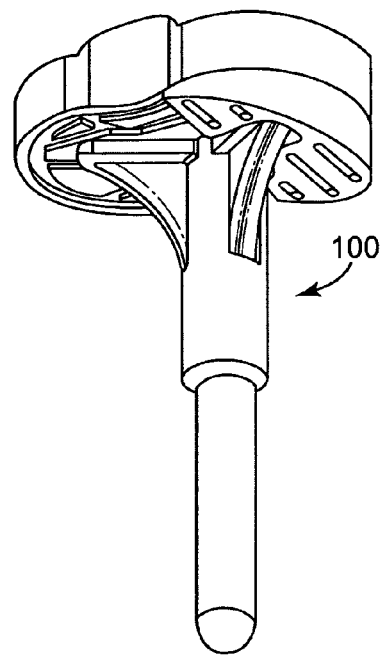
Fig. 13a Fig. 13b
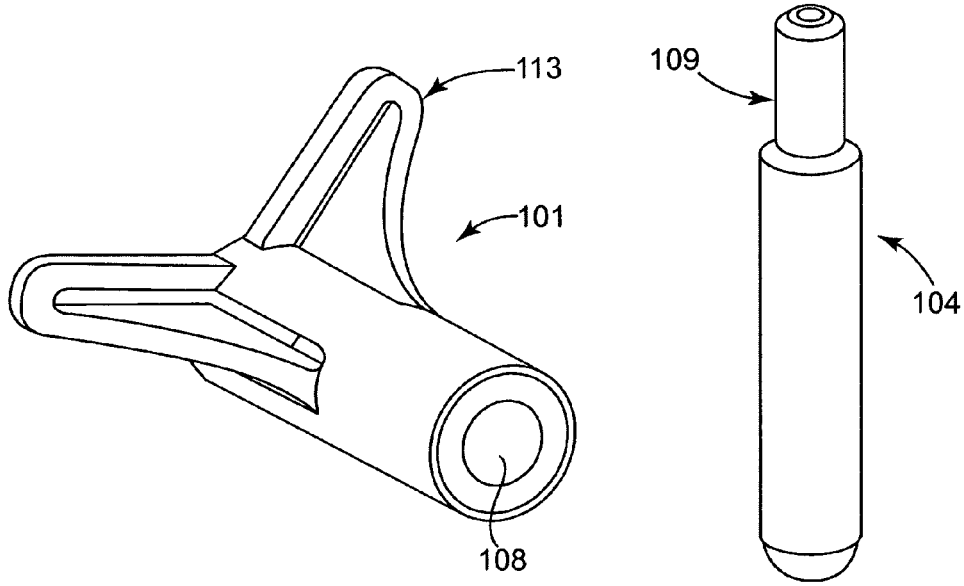
Fig. 14 Fig. 15

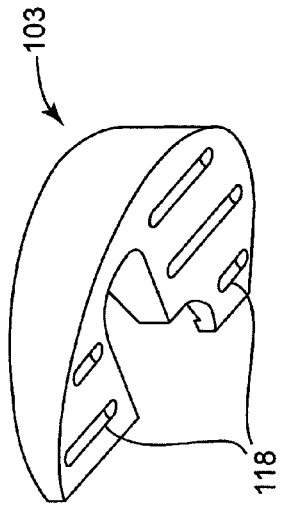
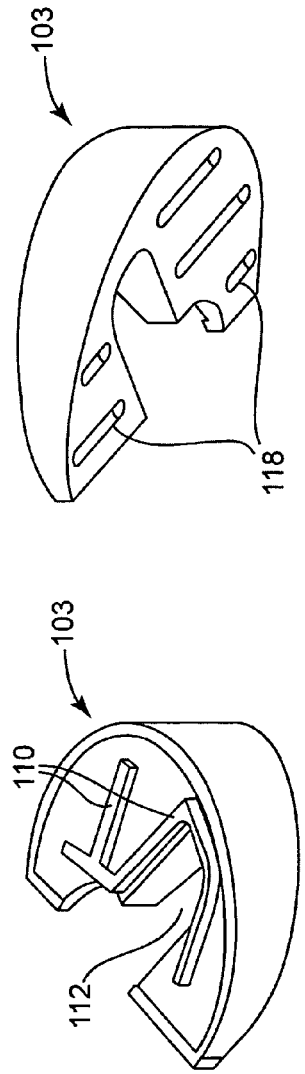
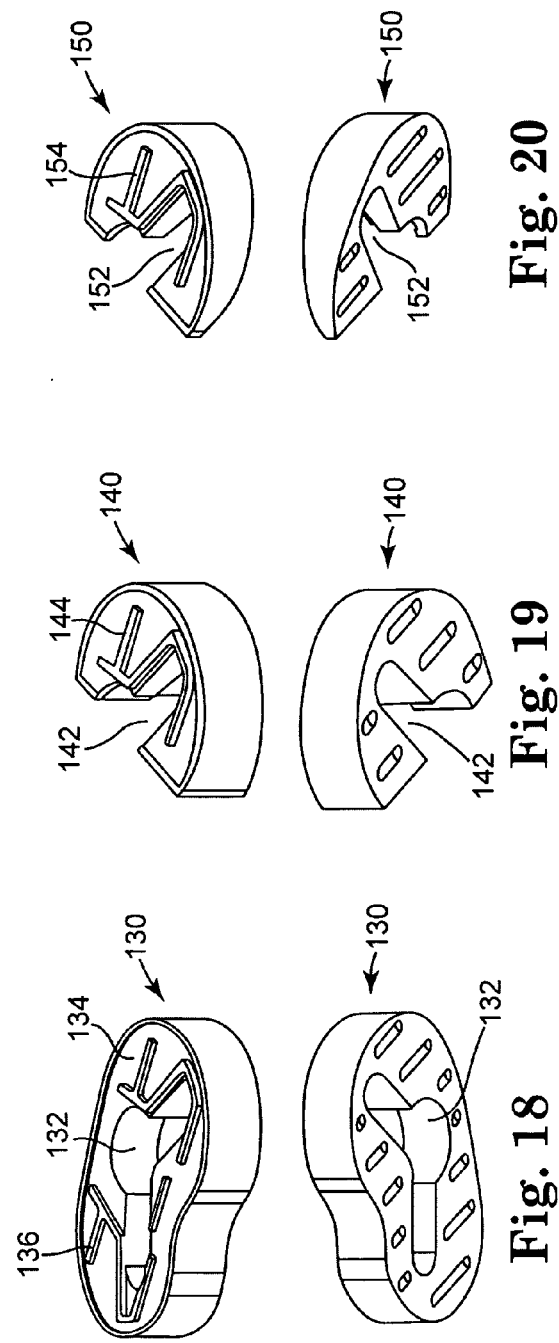

TIBIAL COMPONENT WITH A CONVERSION MODULE FOR A KNEE IMPLANT

CROSS-REFERENCE TO RELATED APPLICATION

The present application claims priority to U.S. Provisional Application No. 60/752,849, filed Dec. 21, 2005, titled "Tibial Component With a Conversion Module for a Knee Implant", the entire contents of which is incorporated herein by reference in its entirety.

TECHNICAL FIELD

The present invention relates to total knee implants. In particular, the invention relates to a polyethylene tibial component with a conversion module that allows the incorporation of a metal extension peg into the assembly.

BACKGROUND

In general, total knee implants consist of three components: a femoral component, a tibial component, and a patellar component. Tibial components often fall into the categories of either metal-backed (modular) or all-polyethylene (also referred to as "all-poly") tibial components. Metal-backed or modular tibial components often have a metal tray supporting a plastic modular piece that articulates with the femoral component. An all-poly tibial component, as the name implies, is a non-modular one-piece component made entirely of polyethylene plastic.

It has been shown that the long-term results of all-polyethylene tibial components have some advantages over metal-backed tibial components. For example, all-polyethylene components are often cheaper, easier to manufacture, and can exhibit better wear characteristics than metal-backed tibial components. However, in order to add to the stability of the tibial component, such as for revision cases or in cases where there is significant bone loss in the proximal tibia, it can be advantageous to include an extended metal tibial stem or peg in the implant. In many cases, the attachment of such a metal component directly to a polyethylene component can be difficult and may result in unsatisfactory attachment conditions. Thus, it has been known to use a tibial component that includes a polyethylene or other plastic portion with an attached metal backing to allow for attachment of an extended metal tibial stem or peg to the metal backing portion of the tibial component. However, there is a need to provide a knee implant assembly that allows a metal peg to be attached to an all-poly tibial component, thus offering the advantages of both metal-backed and all-poly tibial components.

SUMMARY

The present invention relates to total knee implants that include a metal adaptor or tibial conversion module that allows a metal intramedullary peg to be used in an assembly that includes an all-polyethylene tibial component. The intramedullary peg adds to the stability of the all-poly tibial component, which can be particularly advantageous for revision cases or in cases where there is significant bone loss in the proximal tibia. Plastic or metal blocks and wedges can also be used with the implant assembly to fill bony defects.

The metal adaptor or conversion module can be designed for all-poly tibial components with or without dovetail cuts on the underside. The conversion unit can also be used for all-poly tibial components wherein a ridge along the periphery of the underside has been incorporated which is designed to prevent bone cement from migrating during implant insertion.

In one aspect of the invention, a tibial prosthesis is provided that includes a tibial component including a tray having first and second opposing surfaces and a stem extending from the second surface of the tibial component, a tibial conversion module including a receiver portion defining a stem-receiving cavity for slideable engagement with the stem of the tibial component, wherein the stem of the tibial component is positioned within the stem-receiving cavity at a first end of the receiver portion, and an extension peg engaged with the stem-receiving cavity at a second end of the receiver portion that is opposite the first end of the receiver portion. The tibial component and tibial conversion module are preferably made of different materials, such as polyethylene for the tibial component and metal for the tibial conversion module.

In another aspect of the invention, a tibial prosthesis is provided that includes a tibial component comprising a tray having first and second opposing surfaces and a stem extending from the second surface of the tibial component, a tibial conversion module comprising at least one engagement component slideably engaged with the second surface of the tibial component at a first end of the tibial conversion module, and an extension peg engaged with a second end of the tibial conversion module. The tibial component and tibial conversion module are preferably made of different materials, such as polyethylene for the tibial component and metal for the tibial conversion module.

BRIEF DESCRIPTION OF THE DRAWINGS

The present invention will be further explained with reference to the appended Figures, wherein like structure is referred to by like numerals throughout the several views, and wherein:

FIG. 1 is an exploded perspective view of the components of one embodiment of a knee implant of the present invention;

FIG. 2 is another perspective view of the knee implant components shown in FIG. 1, further including directional arrows to indicate the component locations relative to each other when assembled;

FIG. 3a is a perspective view of a knee implant assembly of the present invention;

FIG. 3b is a bottom perspective view of the knee implant illustrated in FIG. 3a;

FIGS. 13a and 13b are two perspective views of a knee implant assembly, including a tibial wedge on one side of the bottom surface of the tibial component;

FIG. 14 is another perspective view of the conversion module of FIG. 9, showing an opening in the bottom shank;

FIG. 15 is a perspective view of the extension peg of FIG. 9; and

FIGS. 16-20 are perspective views of a variety of embodiments of tibial wedges and/or tibial components that can be used with the knee implant assemblies of the invention.

DETAILED DESCRIPTION

Figure 4:
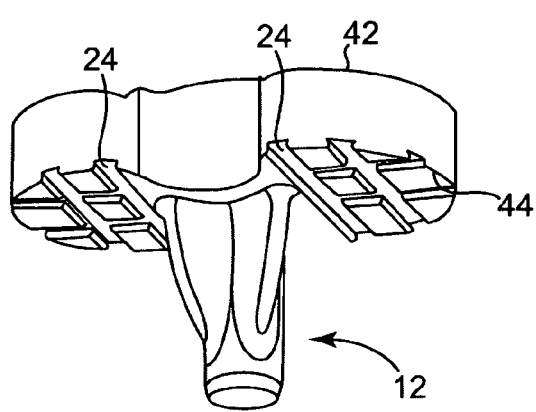
FIG. 4 is a bottom perspective view of one embodiment of the tibial component of the knee implant of the invention.

Referring now to the Figures, wherein the components are labeled with like numerals throughout the several Figures, and initially to FIGS. 1-3b, one exemplary embodiment of a knee implant assembly 10 of the present invention is illustrated. As is best illustrated in the exploded views of FIGS. 1 and 2, the assembly 10 generally includes a tibial component 12, a tibial conversion module or unit 14, and an extension peg 16. FIG. 2 further includes a directional arrow 18 showing the direction the tibial component 12 moves relative to the tibial conversion module 14 to mate with the tibial conversion module 14, and a directional arrow 20 showing the direction the extension peg 16 moves relative to the tibial conversion module 14 to mate with the tibial conversion module 14, which will be described in further detail below. FIGS. 3a and 3b illustrate the knee implant assembly 10 in its assembled configuration.

In accordance with the present invention, the tibial component 12 is preferably made entirely or primarily of polyethylene, and can be manufactured using any known forming techniques, such as molding. It is contemplated, however, that materials other than polyethylene are incorporated into the structure of the tibial component 12. For example, metal particles may be incorporated into the material that makes up the tibial component 12 to provide additional strength to the structure. However, in order to achieve at least some of the desirable properties for which polyethylene may be chosen, the tibial component 12 may be made of entirely of polyethylene.

The tibial conversion module 14 is preferably made entirely or primarily of metal, such as stainless steel or titanium, where it is preferable that the entire module 14 is made of the same metal. However, it is possible that the conversion module 14 is made of more than one material, where certain portions are made from particular materials to give certain strength characteristics to the module 14. The conversion module 14 may be machined or molded into its desired configuration. The module 14 also includes features for engagement with the tibial component 12, which will be described below.

As shown in FIG. 4, the tibial component 12 has a first or top surface 42 and a second or bottom surface 44 that is generally opposite the top surface 42. Surfaces 42, 44 can be generally parallel to each other as shown, or may be offset or angled relative to each other. The bottom surface 44 of the tibial component 12 has multiple grooves 24 that extend generally from one side of the tibial component 12 to its opposite side, although it is contemplated that the grooves extend across only a portion of the tibial component 12 in one or more directions. However, in order to be able to engage with another component in the system in a sliding type of engagement, the grooves 24 can preferably have at least one end that terminates at a face of the tibial component 12. This is particularly advantageous if the grooves 24 have a dovetail configuration, as is illustrated in FIG. 4 so that a mating dovetail shaped component can engage with it. Alternatively, the grooves 24 may be rectangular, curved, or otherwise shaped. The particular design and pattern of the underside grooves 24 may vary from one system to another, but are generally provided for engagement with another component and/or for use as anchoring points or channels for bone cement or other adhering material when the tibial component 12 is implanted. The grooves 24 may extend in one or both directions relative to the length and width of the component 12, and may intersect with each other at one or more locations. Thus, a dovetail configuration is only one of a number of possible configurations for the grooves 24. The number of grooves, the arrangement of the grooves, and the relative length and widths of the grooves may vary slightly or considerably from the grooves 24 illustrated in FIG. 4.

Figure 5:
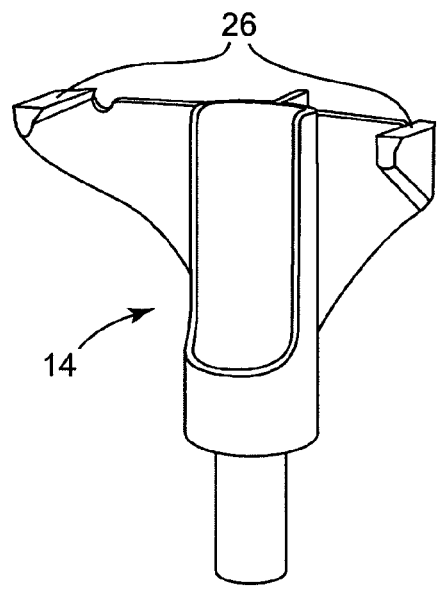
FIG. 5 is perspective view of one embodiment of the tibial conversion module of the invention.
Figure 6:
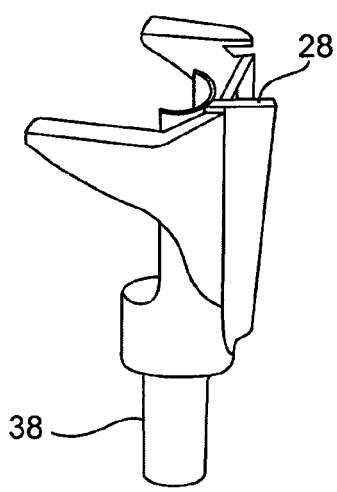
FIG. 6 is a perspective view of one side of the tibial conversion unit shown in FIG. 5.

In the configuration of FIG. 4, the grooves 24 can be used as anchoring points for bone cement, and also provide a means of engaging with or attaching to the tibial conversion module 14. As shown in FIG. 5, the tibial conversion module 14 has pair of skids 26 with a dovetail cross-section that corresponds to the dovetail shape of the grooves 24 on the corresponding tibial component 12. The tibial conversion module 14 preferably also has a locking ramp 28, as shown in FIG. 6, which is used in the structural attachment of the various components, as described below.

Figure 7:
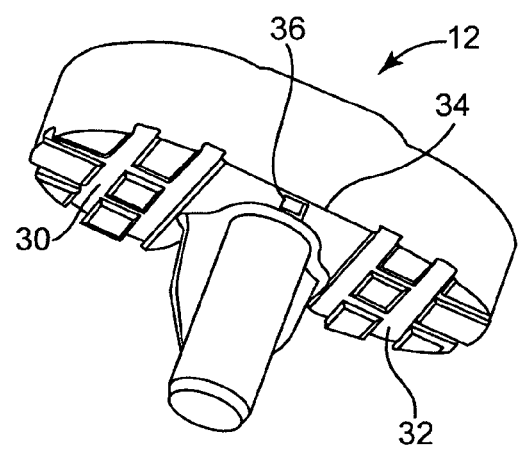
FIG. 7 is another bottom perspective view of an embodiment of the tibial component of the knee implant of the invention.

In one assembly sequence of the invention, the tibial conversion module 14 is assembled onto the tibial component 12 (see FIG. 2) by slideably engaging the skids 26 with grooves 30 and 32 in a direction that is parallel to the second surface 44 of the tibial component 12. Grooves 30 and 32 are provided on the bottom surface of the tibial component 12, which are best shown in FIG. 7. These grooves 30, 32 are specifically spaced and sized for engagement with corresponding skids, such as skids 26. This engagement of the skids 26 in the grooves 30 and 32 prevents the tibial component 12 and the conversion module 14 from being separated in the vertical direction. As the tibial conversion module 14 is slid further onto the tibial component 12, the locking ramp 28 engages a back edge 34 of the tibial component 12. The tibial conversion module 14 and the tibial component 12 are further slid relative to each other until the locking ramp 28 engages with a locking cavity 36 of the tibial component 12, thereby locking the two components together. The locking ramp 28 may include a feature that inhibits or prohibits the disengagement of the locking function once it has been engaged. It is understood, however, that a wide variety of configurations can be used for both the conversion module and tibial component to hold them together, including other mechanical or other types of engagement configurations between the components. It is desirable, however, that the engagement of the components is secure enough that the components cannot come apart, even under a variety of different loading conditions.

Figure 8:
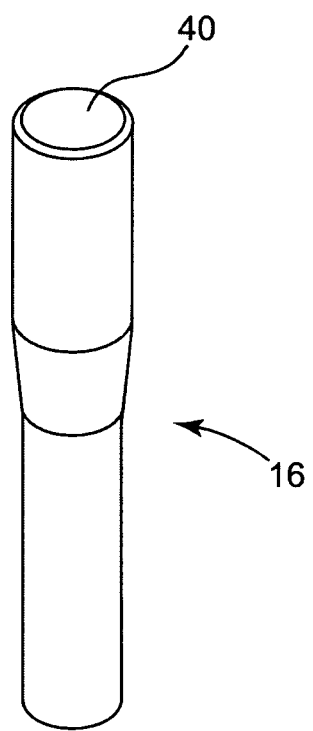
FIG. 8 is a perspective view of an embodiment of the extension peg of the invention.
Figure 9:
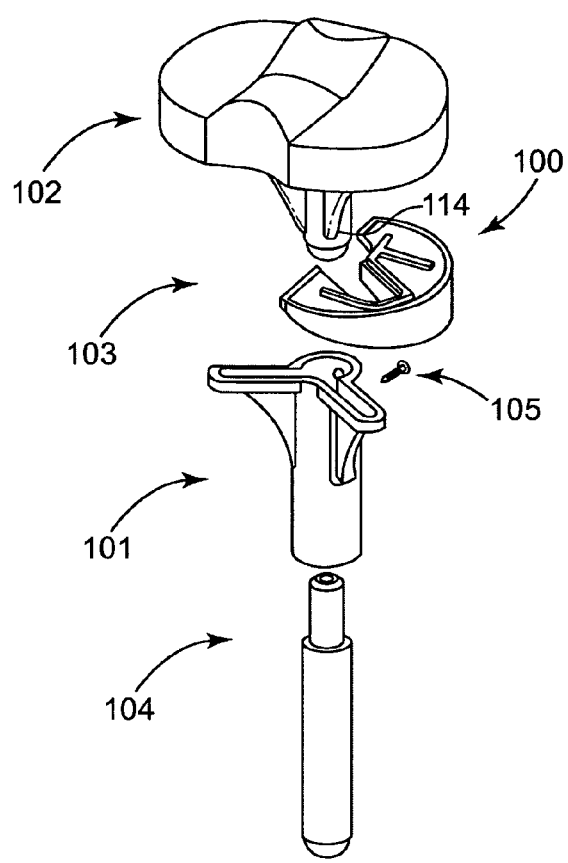
FIG. 9 is an exploded perspective view of the components of another embodiment of a knee implant of the present invention.

When the tibial conversion module 14 and the all-poly tibial component 12 are attached to each other, the tibial conversion module 14 allows the extension peg 16 to be attached to the assembly, as shown in FIGS. 3a and 3b. The tibial conversion module 14 may have a tapered shank 38 (see FIG. 6), which is configured for engagement with a tapered hole 40 in extension peg 16 (see FIG. 8), thereby forming a Morse taper type of connection. Thus, the present invention is able to offer the advantages of both an all-polyethylene tibial component and a metal-backed tibial component. In another alternative connection, the tapered hole 40 can be threaded to mate with threads on the outer surface of extension peg 16 to attach the components to each other. A wide variety of alternative connection configurations can also be used for attachment of the extension peg 16 to the tibial conversion module 14, such as may include pins, clips, screws, and other engagement components and configurations. Further, while this embodiment illustrates the tapered shank 38 of the conversion module 14 as being insertable into the tapered hole 40 of extension peg 16, the components may instead essentially be reversed so that the shank 38 of the conversion module 14 has a hole for internal connection of an extension peg 16, such as with a friction fit, a threaded connection, or another engagement configuration.

FIGS. 9-17 illustrate another exemplary embodiment of a knee implant assembly 100 of the invention and its individual components. Implant assembly 100 generally includes a conversion module 101, a tibial component 102, a tibial wedge 103, and an intramedullary peg 104. The tibial wedge 103 is an optional component of the system and is particularly adaptable for filling bony defects in the proximal tibia.

The conversion module 101 is preferably a metal component that is engageable with an extending post 114 of tibial component 102. The tibial component 102 is preferably made entirely or primarily of polyethylene. The intramedullary (IM) peg 104 is preferably made entirely or partially of metal or another material that provides the desired structural integrity to the assembly. The optional tibial wedge or wedges 103 can be made of polyethylene, metals, plastics, combinations thereof, and the like. Thus, the use of a conversion module 101 allows for an assembly that provides a number of advantages in that the tibial component 102 can be made of polyethylene, yet it can be securely attached to a metal intramedullary peg 104 via the intermediate conversion module 101. It is contemplated, however, that these components may be made of different materials or combinations of materials, and/or that the components may all be made of the same material as each other, as desired. In any case, the materials that make up the components can be selected to provide the desired properties (e.g., strength, weight, and the like) to the final knee implant assembly.

Figure 10:
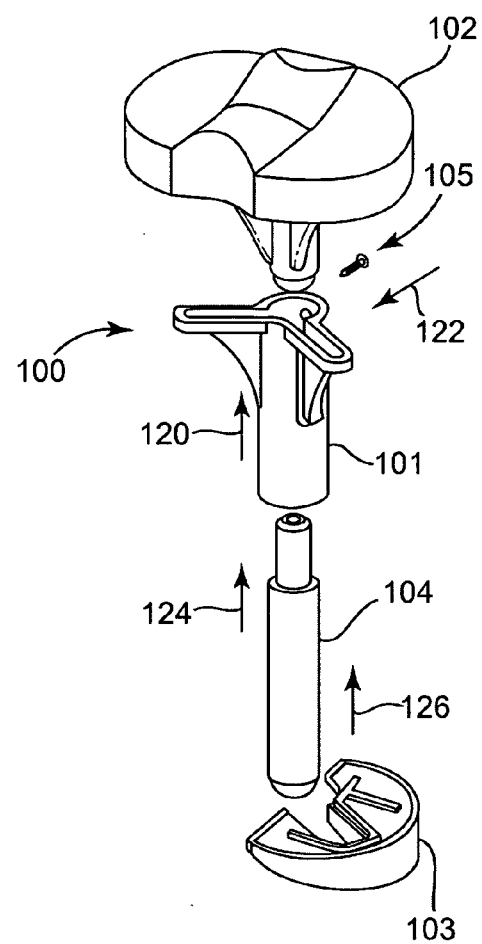
FIG. 10 is another perspective view of the knee implant components shown in FIG. 9, further including directional arrows to indicate the direction components can be moved relative to each other for assembly and to illustrate one exemplary order of steps involved in assembling the knee implant.
Figure 11:
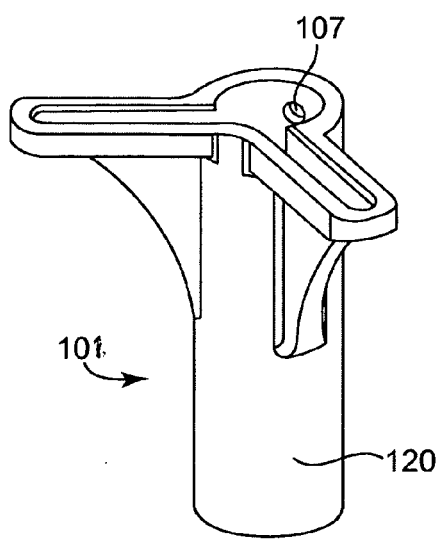
FIG. 11 is a perspective view of the tibial conversion module of FIG. 9.
Figure 12:
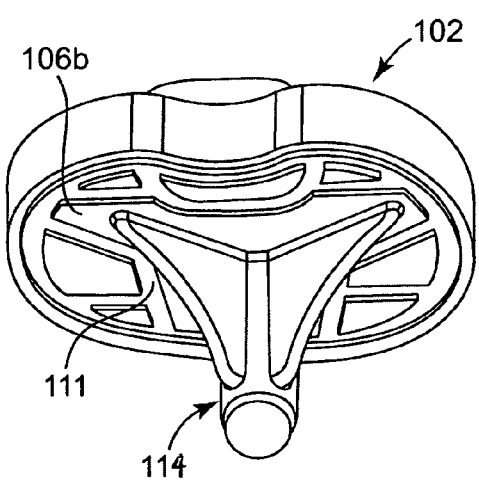
FIG. 12 is a bottom perspective view of the tibial component of FIG. 9.

FIG. 10 shows one exemplary sequence of assembling the different components together into a knee implant assembly 100, where the first step is illustrated with directional arrow 120. In this step, the conversion module 101 is pressed onto the extending post 114 of the tibial component 102 until a surface 106a of conversion module 101 is in contact with a surface 106b of a tray or plate of tibial component 102 (shown in FIGS. 11 and 12). The surfaces 106a and 106b are preferably designed to allow complete or nearly complete contact between them. That is, the surfaces 106a and 106b can be manufactured so that they have surfaces that can be generally or completely flush when they come into contact with each other, which helps to minimize or prevent rotation in the coronal and/or sagittal planes. In the illustrations of FIGS. 11 and 12, the surface 106b of tibial component 102 comprises a number of raised and recessed areas, which can vary widely from that shown; however, the selection of a configuration for the surface 106b is preferably selected or designed to cooperate with a corresponding surface 106a. For one example, the surface 106b can have a portion of its surface that is recessed in an identical or nearly identical pattern to the outer surface shape and size of the surface 106a. In this way, the surface 106a can mate with the surface 106b in the recessed area, thereby providing close contact between the conversion module 101 and the tibial component 102.

A second (optional) step in assembling the knee implant assembly 100 is illustrated with directional arrow 122. In this step, a locking element or screw 105 is threaded, pressed, or otherwise engaged with the assembly of the conversion module 101 and tibial component 102 to secure these pieces to each other. In this embodiment, the conversion module 101 is provided with a mating feature or aperture that can engage with a pin or set screw 105 to lock the conversion module 101 and the tibial component 102 to each other. This attachment of the module 101 to the tibial component 102 may be accomplished in a number of different ways, such as by friction or interference fit between the two components, for example. These alternative attachment methods may be used instead of or in addition to using a device such as a locking element or screw. That is, in one embodiment, the conversion module 101 can act like a pocket or pouch for accepting tibial component 102 and no other attachment mechanisms are used. This is possible because the main forces will be downward on the assembly after it is implanted in a patient, thereby pressing the tibial component 102 into conversion module 101.

A third step in assembling the knee implant assembly 100 is illustrated with directional arrow 124. In this step, the intramedullary peg 104 is pressed or otherwise secured to the conversion module 101 by interference fit or threaded fasteners, for example. As with the embodiment of FIG. 1, this attachment may be accomplished using a number of different techniques and configurations that provide for secure attachment of the components under a variety of loading conditions. In another example, the conversion module 101 has a tapered hole 108, shown in FIG. 14, which can mate with a tapered shank 109 of the intramedullary peg 104 (see FIG. 15), which thereby forms a Morse taper type of connection.

A fourth step in assembling the knee implant assembly 100 is illustrated with directional arrow 126. In this optional step, a desired number of tibial wedges 103 can be slid or otherwise moved onto the assembly until the wedge or wedges 103 come in contact with the bottom surface of the tibial component 102. The wedge or wedges 103 can be secured to the bottom surface of the tibial component 102, as desired and as will be discussed in further detail below. The tibial wedge or wedges 103 are selected or designed for use depending on the size and type of bony defect in the proximal tibia that needs to be filled.

It is understood that this assembly sequence described above is intended to be one exemplary assembly sequence, and that the steps may be performed in a different order. For example, tibial wedges 103 may be secured to the tibial component 102 prior to the intramedullary peg 104 being secured to conversion module 101. In addition, because one or more tibial wedges 103 may or may not be necessary for a particular patient, this step may be performed multiple times with wedges of the same or different sizes and shapes, or may be not be performed at all if wedges are not needed.

It should be noted that the embodiments of FIGS. 2 and 10 illustrate different ways of attaching the tibial components 12 and 102 to the conversion modules 14 and 101, respectively, where the entire assemblies can be embedded in bone cement when implanted in the patient. That is, the portion of the assemblies 10 and 100 from the bottom surface of tibial component 12 or 102 down to the extension peg 16 or intramedullary peg 104 can be embedded in bone cement. In this situation, other than the locking mechanisms discussed above, the tibial components 12 or 102 will be connected or attached to the conversion modules 14 or 101, respectively, due to the properties of the bone cement in which they are embedded.

Without the conversion module 101, the tibial component 102 can function as a standard all-polyethylene tibial component 102 in a standard total knee implant. However, when the conversion module 101 of the invention, which is preferably metal, and the polyethylene tibial component 102 are assembled or connected to each other, the conversion module 101 allows the intramedullary peg 104 to be attached to the assembly as shown in FIGS. 13a and 13b.

As set out above, one or more tibial wedges can be used as an optional component to fill bony defects in the proximal tibia, where the wedges can partially or completely cover the bottom face of the tibial component. With particular reference to the tibial wedge 103 of FIGS. 16 and 17, the top surface of the wedge 103 has multiple ridges 110 that can fit into grooves 111 of tibial component 102 (see FIG. 12). These ridges 110 can minimize or prevent relative movement between the tibial component 102 and each tibial wedge 103. The width of the ridges 110 can be at least slightly smaller than the width of the grooves 111 so that the space formed can be filled with cement, although it is also possible to provide a tighter friction fit between the ridges and grooves. However, if a space is provided, such space between the ridges 110 and the grooves 111 can be filed with bone cement or the like during assembly of tibial component 102 and tibial wedge 103, which can help to maintain a secure attachment between the components.

Tibial wedge 103 can further include a cavity 112 that corresponds with the shape of the flanges 113 of conversion module 101 shown in FIG. 14. These flanges 113 are wider than a cylindrical portion 120 of conversion module 101 and comprise the face 106a described above. The tibial wedge 103 can further include at least one groove 118 on the underside of tibial wedge 103, at least some of which can be used as anchor points for bone cement, if desired.

FIGS. 18-20 illustrate top and bottom perspective views of three exemplary types of tibial wedges that can be used with the knee implant assemblies of the invention. In particular, FIG. 18 illustrates a "full-wedge" configuration of a wedge 130. Wedge 130 includes a central aperture 132 that is shaped and sized to fit over the flanges of a conversion module, such as flanges 113 of conversion module 101. In this way, a top surface 134 of wedge 130 can contact the bottom surface of tibial component 102 when assembled. This type of wedge can further include at least one ridge 136 that extends from the top surface 134 for contact and/or engagement with at least one corresponding groove on the bottom surface of tibial component 102.

FIG. 19 illustrates a "hemi-wedge" configuration of a wedge 140. Wedge 140 is essentially the same as tibial wedge 103 described above, in that it includes a cavity 142 to mate with a flange 113 of conversion module 101. FIG. 20 illustrates a more triangular-shaped wedge 150, which also includes a cavity 152 to mate with a flange 113 of conversion module 101. As shown, the top and bottom surfaces of wedge 150 are not parallel to each other, but instead form a triangular or somewhat pie-shaped wedge, which can accommodate certain types of bony defects that are not accommodated by a wedge having parallel opposing surfaces. Both of the wedges 140, 150 can also include at least one ridge 144, 154, respectively, that extend from one surface of their respective wedges for contact and/or engagement with at least one corresponding groove on the bottom surface of a tibial component with which they will come in contact. In any case, a wide variety of wedges can be used, which are selected for use depending on the needs of each particular patient. The wedges can be made of polyethylene, metals, plastics, combinations thereof, and the like, and can be constructed by molding, forming, or other manufacturing techniques specifically chosen to cooperate with the material chosen.

In the embodiments of the invention described above, the tibial component is generally described as being entirely made of polyethylene, while the conversion module and extension peg are described as being made entirely of metal. However, it is considered to be within the scope of the invention that any of these components may include multiple materials, which are designed to function together to provide an overall desired strength for the assembly. For example, the conversion module may be constructed to be partially made of polyethylene and/or another non-metal material, as long as it can provide the desired structural strength to the knee implant assembly.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A tibial prosthesis, comprising:
   a tibial component comprising a tray having first and second opposing surfaces, a front edge, a back edge, and a stem extending from the second surface, wherein the first surface comprises concave regions configured to articulate with condyles of a femoral component when implanted in a patient, wherein the second surface comprises at least one engagement channel extending from the front edge toward the back edge, and wherein the stem is configured for anchoring the tibial component in the tibia of a patient;
   a tibial conversion module comprising:
      a receiver portion comprising a first end and defining a stem-receiving cavity at the first end for slideable engagement with the stem of the tibial component;
      at least one engagement member comprising a length at a first end of the receiving portion; and
      a shank extending in a longitudinal direction relative to the stem-receiving cavity at a second end of the receiver portion,
      wherein each engagement member is slideably engageable along its length in a direction that is parallel to the second surface with one of the engagement channels of the tibial component, and wherein the stem of the tibial component is positionable within the stem-receiving cavity at a first end of the receiver portion by sliding movement of the tibial conversion module in a direction that is parallel to the second surface of the tibial component; and
   an extension peg configured for anchoring the tibial component in the tibia of a patient, distinct from the tibial component and the tibial conversion module, and engaged with the shank.

2. The tibial prosthesis of claim 1, wherein the tibial component comprises a first material and the tibial conversion module comprises a second material that is different from the first material.

3. The tibial prosthesis of claim 2, wherein the first material is polyethylene.

4. The tibial prosthesis of claim 3, wherein the second material is metal.

5. The tibial prosthesis of claim 2, wherein the extension peg comprises the second material.

6. The tibial prosthesis of claim 2, wherein the second material is metal.

7. The tibial prosthesis of claim 1, further comprising a securing mechanism engaged with the extension peg and the tibial conversion module for securing the extension peg to the tibial conversion module.

8. The tibial prosthesis of claim 1, wherein the tibial conversion module further comprises a top surface at the first end of the receiver portion that is in contact with the second surface of the tibial component.

9. The tibial prosthesis of claim 1, wherein the stem-receiving cavity is defined by a concave wall having first and second ends spaced from each other at opposite ends of an arc.

10. A tibial prosthesis, comprising:
a tibial component comprising a tray having first and second opposing surfaces, a front edge, a back edge, and a stem extending from the second surface of the tibial component, wherein the second surface comprises at least one engagement feature extending from the front edge toward the back edge, wherein the first surface comprises concave regions configured to articulate with condyles of a femoral component when implanted in a patient, and wherein the stem is configured for anchoring the tibial component in the tibia of a patient;
a tibial conversion module comprising:
at least one engagement component slideably engageable in a direction that is parallel to the second surface with the engagement feature of the second surface of the tibial component at a first end of the tibial conversion module;
a stem-receiving cavity defined by an arc-shaped wall that extends in a longitudinal direction at the first end of the tibial conversion module, wherein the stem of the tibial component is positionable within the stem-receiving cavity by sliding movement of the tibial conversion module in a direction that is parallel to the second surface of the tibial component; and
a shank extending in a longitudinal direction relative to the stem-receiving cavity at a second end of the tibial conversion module; and
an extension peg configured for anchoring the tibial component in the tibia of a patient, distinct from the tibial component and the tibial conversion module, and engaged with the shank at the second end of the tibial conversion module.

11. The tibial prosthesis of claim 10, wherein the tibial component comprises a first material and the tibial conversion module comprises a second material that is different from the first material.

12. The tibial prosthesis of claim 11, wherein the first material is polyethylene.

13. The tibial prosthesis of claim 12, wherein the second material is metal.

14. The tibial prosthesis of claim 11, wherein the extension peg comprises the second material.

15. The tibial prosthesis of claim 10, wherein the at least one engagement feature of the second surface of the tibial component comprises at least one groove, and wherein the at least one engagement component of the tibial conversion module comprises at least one skid that is slidebly engageable with the at least one groove of the tibial component.

16. The tibial prosthesis of claim 10, wherein the tibial conversion module further comprises a locking ramp that is engageable with a portion of the tibial component.

17. The tibial prosthesis of claim 16, wherein the second surface of the tibial component further comprises a locking cavity for engagement with the locking ramp of the tibial conversion module.

* * * * *